(12) United States Patent
Longoria et al.

(10) Patent No.: US 11,426,301 B2
(45) Date of Patent: Aug. 30, 2022

(54) WEARABLE MEDICAL DEVICE

(71) Applicants: Kaei Longoria, League City, TX (US); Matthew Longoria, League City, TX (US)

(72) Inventors: Kaei Longoria, League City, TX (US); Matthew Longoria, League City, TX (US)

( * ) Notice: Subject to any disclaimer, the term of this patent is extended or adjusted under 35 U.S.C. 154(b) by 0 days.

(21) Appl. No.: 16/521,258

(22) Filed: Jul. 24, 2019

(65) Prior Publication Data

US 2021/0022905 A1    Jan. 28, 2021

(51) Int. Cl.
*A61F 5/00* (2006.01)
*A61F 5/37* (2006.01)

(52) U.S. Cl.
CPC .................... *A61F 5/3738* (2013.01)

(58) Field of Classification Search
CPC ...... A61F 5/373; A61F 5/3723; A61F 5/3715; A61F 5/3738
See application file for complete search history.

(56) References Cited

U.S. PATENT DOCUMENTS

| | | | | |
|---|---|---|---|---|
| 1,808,422 A | * | 6/1931 | MacDonald | A61F 5/05808 602/4 |
| 4,041,940 A | * | 8/1977 | Frankel | A61F 5/0585 602/26 |
| 4,437,459 A | * | 3/1984 | Slavetskas | A61F 5/3738 128/DIG. 15 |
| 4,489,716 A | * | 12/1984 | Blackwood | A61F 5/373 602/20 |
| 4,625,719 A | * | 12/1986 | Chambers | A61F 5/3738 128/DIG. 15 |
| 5,848,956 A | * | 12/1998 | Grettner | A61F 5/3738 482/69 |
| 6,595,937 B1 | * | 7/2003 | Moon | A61F 5/05841 602/20 |
| 2004/0215119 A1 | * | 10/2004 | Avon | A61F 5/3738 602/4 |
| 2013/0012847 A1 | * | 1/2013 | Lowe | A61H 9/0092 601/18 |

* cited by examiner

*Primary Examiner* — Steven O Douglas

(57) ABSTRACT

The present invention relates to a wearable medical device for immobilizing an appendage. More specifically, the apparatus utilizes absorbent and moisture wicking material thereby preventing accumulation of moisture and decrease chafing during use of the medical device. The apparatus is also intended to allow a user to install and remove the sling liner by using one hand.

10 Claims, 1 Drawing Sheet

WEARABLE MEDICAL DEVICE

FIELD OF INVENTION

The present invention is generally related to a wearable medical device to immobilize an appendage.

BACKGROUND OF INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in-and-of-themselves may also be inventions.

This specification recognizes that existing wearable medical devices are complex and do not allow the users to immobilize or adjust the medical device easily. Additionally, it is recognized in this specification that the existing medical devices do not prevent accumulation of moisture and fail to control chafing. Furthermore, it is recognized in this specification that the existing medical devices do not prevent the build-up of odor caused by the bacteria on the device.

Thus, in view of the above, there is a long-felt need in the industry to address the aforementioned deficiencies and inadequacies.

SUMMARY OF THE INVENTION

A wearable medical device to immobilize an appendage is provided substantially, as shown in and/or described in connection with at least one of the figures, and as set forth more completely in the claims. A shoulder sling designed to immobilize an arm will be primarily used to illustrate the apparatus, but it is recognized that the apparatus could be deployed on any immobilizing medical device. The use of a shoulder sling in this specification should not be used to limit the scope of the invention, but merely to help enable the use of the apparatus.

The wearable shoulder device includes a sling, a sling liner, at least one connective means, and padding. The sling liner is having a predefined length attached with a medical device. The sling liner is made of an absorbent and moisture wicking material. In one embodiment the absorbent and moisture wicking material is terry cloth. Constructing the sling liner out of an absorbent and moisture wicking material prevents an accumulation of moisture and decreases chafing. The connective means is configured with the sling liner to attach to the medical device. The connective means allows a user to install and remove the sling liner by using one hand. In a preferred embodiment the connective means is hook and loop tape. In another embodiment the connective means is a series of magnets. The padding is placed between the sling liner and the sling to provide comfort and support to the arm of the user.

In another embodiment, the padding is inserted into the liner in a similar manner as a pillow would be inserted into a pillowcase and then attached to the medical device.

In an aspect, the connective means prevents the absorbent material from shifting during installation of the sling liner and duration usage of the sling liner.

In an aspect, the predefined length of the sling liner is adjustably set by cutting, folding, or rolling the sling liner according to the length of an arm of the user and size of the medical device.

In an aspect, the connective means allows the user to remove the sling liner for washing and prevents the buildup of odor-causing bacteria on the wearable medical device.

These features and advantages of the present disclosure may be appreciated by reviewing the following description of the present disclosure, along with the accompanying figures wherein like reference numerals refer to like parts.

BRIEF DESCRIPTION OF DRAWINGS

The accompanying drawings illustrate the embodiments of devices, systems, methods, and other aspects of the disclosure. Any person with ordinary skills in the art will appreciate that the illustrated element boundaries (e.g., boxes, groups of boxes, or other shapes) in the figures represent an example of the boundaries. In some examples, one element may be designed as multiple elements, or multiple elements may be designed as one element. In some examples, an element shown as an internal component of one element may be implemented as an external component in another and vice versa. Furthermore, the elements may not be drawn to scale.

Various embodiments will hereinafter be described in accordance with the appended drawings, which are provided to illustrate, not limit, the scope, wherein similar designations denote similar elements, and in which.

DETAILED DESCRIPTION

The present disclosure is best understood with reference to the detailed figures and description set forth herein. Various embodiments have been discussed with reference to the figures. However, those skilled in the art will readily appreciate that the detailed descriptions provided herein with respect to the figures are merely for explanatory purposes, as the methods and systems may extend beyond the described embodiments. For instance, the teachings presented and the needs of a particular application may yield multiple alternative and suitable approaches to implement the functionality of any detail described herein. Therefore, any approach may extend beyond certain implementation choices in the following embodiments.

References to "one embodiment," "at least one embodiment," "an embodiment," "one example," "an example," "for example," and so on indicate that the embodiment(s) or example(s) may include a particular feature, structure, characteristic, property, element, or limitation but that not every embodiment or example necessarily includes that particular feature, structure, characteristic, property, element, or limitation. Further, repeated use of the phrase "in an embodiment" does not necessarily refer to the same embodiment.

Figure 2:
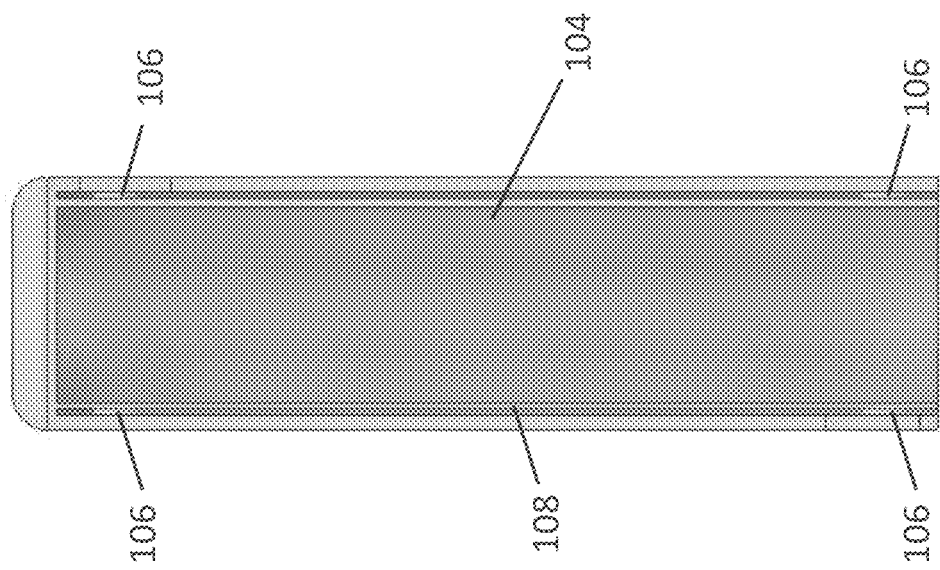
FIG. 2 illustrates a top view of a wearable medical device to immobilize an appendage, in accordance with at least one embodiment.
Figure 1:
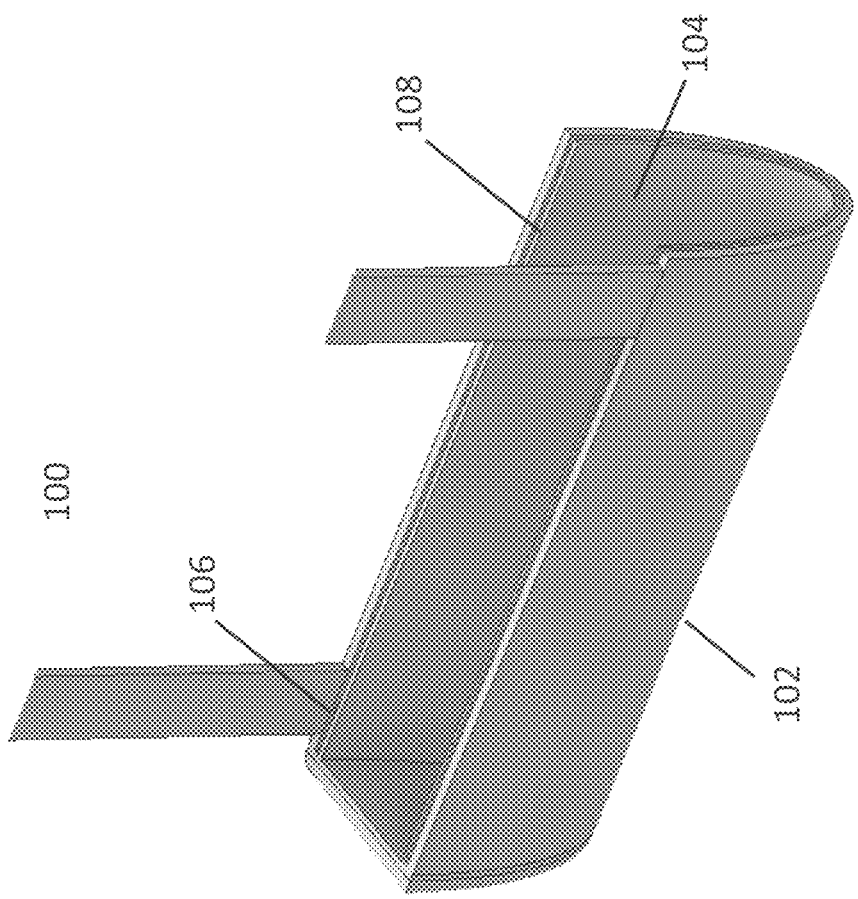
FIG. 1 illustrates an isometric view of a wearable medical device to immobilize an appendage, in accordance with at least one embodiment.

Methods of the present invention may be implemented by performing or completing manually, automatically, or a combination thereof, selected steps or tasks. The term "method" refers to manners, means, techniques and procedures for accomplishing a given task including, but not limited to, those manners, means, techniques, and procedures either known to, or readily developed from known manners, means, techniques and procedures by practitioners of the art to which the invention belongs. The descriptions, examples, methods, and materials presented in the claims and the specification are not to be construed as limiting but rather as illustrative only. Those skilled in the art will envision many other possible variations within the scope of the technology described herein.

FIG. 1 illustrates a wearable medical device 100 to immobilize a shoulder, in accordance with at least one embodiment. The wearable medical device 100 includes a sling 102, a sling liner 104, at least one connective means 106, and a padding 108. The sling 102 and sling liner 104 have a predefined length attached with the medical device. In an embodiment, the predefined length of the sling liner is adjustably set by cutting, folding, or rolling the sling liner according to the length of an arm of the user and size of the medical device. The sling liner 104 is made of an absorbent and moisture wicking material in order to prevent accumulation of moisture and decrease chafing during use The connective means 106 is configured with the sling liner 104 to attach the sling liner to the sling so that it is incorporated into the medical device. In an embodiment, the connective means 106 prevents the sling liner 104 from shifting during installation and while using the medical device 100. The connective means 106 allows a user to install and remove the sling liner 104 by using one hand. The padding 108 is placed between the sling liner 104 and the appendage to support the arm of the user. In one embodiment as shown in FIG. 1 and FIG. 2, the padding 108 is inserted into the sling liner like a pillow might be placed into a pillowcase then attached to the sling as a unit via the connective means.

In an embodiment, the connective means 106 allows the user to remove the sling liner 104 for washing and prevents the buildup of odor-causing bacteria on the wearable medical device 100.

In one embodiment, the connective means 106 is further comprised of hook and loop tape. In another embodiment, the connective means 106 is further comprised of magnets. In yet another embodiment, the connective means 106 is further comprised of a zipper. In another embodiment, the connective means 106 is further comprised of buttons.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms enclosed. On the contrary, the intention is to cover all modifications, alternative constructions, and equivalents falling within the spirit and scope of the invention, as defined in the appended claims. Thus, it is intended that the present invention cover the modifications and variations of this invention, provided they are within the scope of the appended claims and their equivalents.

The invention claimed is:

1. A wearable medical device liner, the wearable medical device liner comprises:
   a predefined length;
   wherein the predefined length of the wearable medical device liner is adjustably set by cutting, folding, or rolling the wearable medical device liner according to the length of an arm of the user and size of a medical device;
   a connective means configured with the wearable medical device liner to removably attach to the medical device;
   a padding;
   wherein the padding is further comprised of a connective means to removably attachment and placed between the wearable medical device liner and the wearable medical device.

2. The wearable medical device liner according to claim 1, wherein the wearable medical device liner is made of absorbent and moisture wicking material in order to prevent accumulation of moisture and decrease chafing during use.

3. The wearable medical device liner according to claim 1, wherein the connective means prevents the wearable medical device liner from shifting during installation into and during usage of the medical device.

4. The wearable medical device liner according to claim 1, wherein the connective means allows a user to install and remove the wearable medical device liner by using one hand.

5. The wearable medical device liner according to claim 1, wherein the connective means allows the user to remove the wearable medical device liner for washing and prevents the buildup of odor-causing bacteria on the wearable medical device and the wearable medical device liner.

6. The wearable medical device liner according to claim 1, wherein the padding is inserted into and enveloped by the wearable medical device liner.

7. The wearable medical device liner according to claim 1, wherein the connective means is further comprised of a hook and loop tape.

8. The wearable medical device liner according to claim 1, wherein the connective means is further comprised of a least one set of magnets.

9. The wearable medical device liner according to claim 1, wherein the connective means is further comprised of a zipper.

10. The wearable medical device liner according to claim 1, wherein the connective means is further comprised of at least one button.

* * * * *